(12) United States Patent
Phillips et al.

(10) Patent No.: US 10,545,162 B2
(45) Date of Patent: Jan. 28, 2020

(54) ALIGNMENT SYSTEM FOR CUVETTE SEGMENTS ON CLINICAL CHEMISTRY INSTRUMENTS

(71) Applicant: Siemens Healthcare Diagnostics Inc., Tarrytown, NY (US)

(72) Inventors: Donald Phillips, Newark, DE (US); Tan Bui, Middletown, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 16/319,292

(22) PCT Filed: Jul. 19, 2017

(86) PCT No.: PCT/US2017/042936
§ 371 (c)(1),
(2) Date: Jan. 18, 2019

(87) PCT Pub. No.: WO2018/017766
PCT Pub. Date: Jan. 25, 2018

(65) Prior Publication Data
US 2019/0242920 A1 Aug. 8, 2019

Related U.S. Application Data

(60) Provisional application No. 62/365,298, filed on Jul. 21, 2016.

(51) Int. Cl.
*G01N 35/04* (2006.01)
*G01N 35/02* (2006.01)

(52) U.S. Cl.
CPC .......... *G01N 35/04* (2013.01); *G01N 35/025* (2013.01); *G01N 2035/0444* (2013.01); *G01N 2035/0491* (2013.01)

(58) Field of Classification Search
CPC ... G01N 2035/0443; G01N 2035/0444; G01N 35/025; G01N 35/04; G01N 2035/0448;
(Continued)

(56) References Cited

U.S. PATENT DOCUMENTS 3,555,284 A 1/1971 Anderson
4,090,791 A * 5/1978 Siddiqi ................ G01N 21/253
356/244

(Continued)

FOREIGN PATENT DOCUMENTS

GB 2083617 A 3/1982

OTHER PUBLICATIONS

PCT International Search Report and Written Opinion dated Oct. 18, 2017 (7 Pages).
(Continued)

*Primary Examiner* — Steven Whitesell Gordon

(57) ABSTRACT

A method for aligning a reaction ring in an analyzer system using a gauge vertical reaction ring comprising at least one end slot includes inserting a light beam gauge into an aperture operable to hold the light beam gauge at a height corresponding to a photometer included in the analyzer system. The gauge vertical reaction ring is rotated on the reaction ring until the light beam gauge engages the end slot to confirm alignment of the reaction ring with the photometer.

19 Claims, 9 Drawing Sheets

(58) Field of Classification Search
CPC .... G01N 2035/0491; G01N 2035/0439; B01L 2200/025
USPC ......................................................... 422/64
See application file for complete search history.

(56) References Cited

U.S. PATENT DOCUMENTS

| | | | | |
|---|---|---|---|---|
| 4,123,173 | A | * | 10/1978 | Bullock ................ B04B 5/0407 356/246 |
| 4,234,538 | A | * | 11/1980 | Ginsberg ............. G01N 21/253 250/226 |
| 4,676,952 | A | | 6/1987 | Edelmann et al. |
| 4,855,110 | A | | 8/1989 | Marker et al. |
| 2003/0021734 | A1 | | 1/2003 | Vann et al. |
| 2011/0064543 | A1 | * | 3/2011 | Nuotio ................. G01N 35/025 414/160 |
| 2011/0255090 | A1 | | 10/2011 | Harada et al. |

OTHER PUBLICATIONS

Extended EP Search Report dated Oct. 16, 2019 of corresponding European Application No. 17831832.5, 4 Pages.

* cited by examiner

ALIGNMENT SYSTEM FOR CUVETTE SEGMENTS ON CLINICAL CHEMISTRY INSTRUMENTS

CROSS-REFERENCE TO RELATED APPLICATIONS

This application claims the benefit of U.S. Provisional Application Ser. No. 62/365,298 filed Jul. 21, 2016, which is incorporated herein by reference in its entirety.

TECHNICAL FIELD

The present invention relates generally to methods, systems, and apparatuses for aligning cuvette segments on clinical chemistry instruments. The technology described herein may be integrated into, for example, automated in-vitro diagnostics (IVD) systems to ensure optimal cuvette placement for performing photometric measurements.

BACKGROUND

IVD allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers ("analyzers") onto which fluid containers, such as tubes or vials, containing patient samples, have been loaded.

One component of the analyzer system is a reaction turntable that includes one or more reaction rings. Each reaction ring is arranged into multiple segments, with each segment containing multiple reaction vessels or "cuvettes." Photometer readings are taken at uniform spacing to calculate absorbance measurement in each cuvette. In order to acquire precise measurements, the cuvette must be properly aligned to the photometer light beam. In conventional systems, cuvettes are adjusted vertically by adding shims to align with the top of the cuvette segment mounting ring surface with the screw head. This adjustment requires technique, and does not account for additional tolerances of the segment and cuvettes. Moreover, such adjustments are typically made by visual inspection of the beam on the cuvette window, which does not provide optimum positioning of the window.

SUMMARY

Embodiments of the present invention address and overcome one or more of the above shortcomings and drawbacks by providing methods, systems, and apparatuses related to the alignment of cuvette segment on clinical chemistry analyzers. The reaction ring is part of the analyzer to which first the vertical gauge is applied to set the proper height by inserting the light beam gauge into the aperture and rotating the reaction ring to see if the light beam gauge will engage the end slot in the ends of the reaction ring gauge. Once that height is properly adjusted, the ring may be indexed with the light beam gauge retracted to make sure that it will still be able to insert into the holes equally spaced across the reaction ring gauge after each index. The reaction ring gauge is then removed and replaced with a production cuvette segment assembly which then is marked in the optical window areas by rotating the light beam gauge against the actual cuvette windows so it can be visually inspected upon removal to confirm proper alignment for performing measurements during production.

According to one aspect of the present invention, a system for aligning a reaction ring in an analyzer system includes a gauge vertical reaction ring and a light beam gauge. The gauge vertical reaction ring is installable on the reaction ring and comprises openings at positions corresponding to optical areas associated with cuvettes in a cuvette segments assembly. The light beam gauge comprises an end portion insertable into the openings. In some embodiments, the system further includes a bracket light source photo configured to hold the light beam gauge at a height corresponding to a light source center axis corresponding to a photometer included in the analyzer system. Additionally, the system may include an aperture photometer configured to hold the light beam gauge in the bracket light source photo and a ring lock aperture configured to secure the aperture photometer within the bracket light source photo. In some embodiments, the gauge vertical reaction ring further comprises one or more end slots operable to engage the light beam gauge when the light beam gauge is placed in the bracket light source photo and the gauge vertical reaction ring is rotated on the reaction ring.

According to another aspect of the present invention, a method for aligning a reaction ring in an analyzer system using a gauge vertical reaction ring at least one end slot includes inserting a light beam gauge into an aperture operable to hold the light beam gauge at a height corresponding to a photometer included in the analyzer system. The gauge vertical reaction ring is rotated on the reaction ring until the light beam gauge engages the end slot to confirm alignment of the reaction ring with the photometer.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawing. For the purpose of illustrating the invention, there is shown in the drawing embodiments that are presently preferred, it being understood, however, that the invention is not limited to the specific instrumentalities disclosed. Included in the drawings are the following Figures.

DETAILED DESCRIPTION

The following disclosure describes the present invention according to several embodiments directed at methods, systems, and apparatuses related to the alignment of cuvette segment on clinical chemistry instruments. Briefly, the technology described herein provides a visual marking on the cuvette window to verify the light beam position. A lamp mounting bracket provides the location of the light beam used for photometric analysis. This lamp mounting bracket is utilized to hold a light beam gauge in position to provide marking on a cuvette window. Thus, the process described herein enhances IVD system results by ensuring that the reaction ring is set at the optimum height to be used with all future cuvette segments that are put on the instrument. This process may be performed, for example, during manufacturing to set the height of the reaction ring when the instrument is built or in the event that the radial drive motor needs to be replaced in the field.

Figure 1:
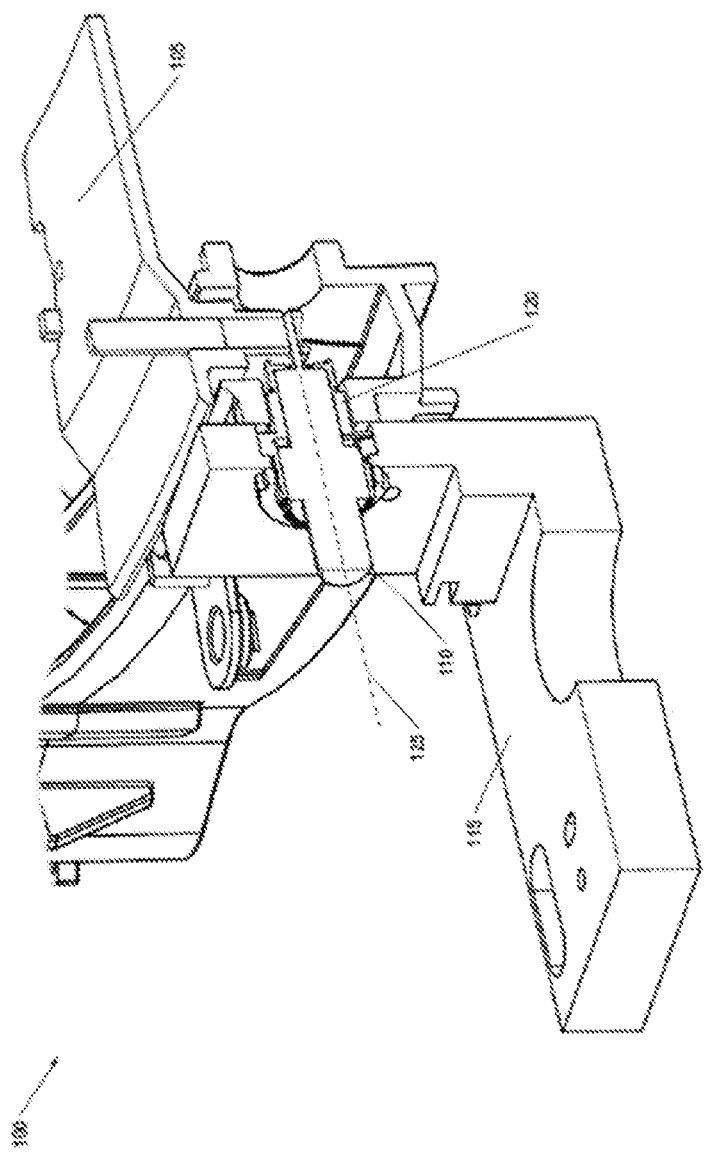
FIG. 1 illustrates a system that may be used to perform cuvette segment alignment, according to some embodiments.

FIG. 1 illustrates a cross-section view of a system 100 that may be used to perform cuvette segment alignment, according to some embodiments. The system 100 adjusts cuvettes to proper vertical positioning for reading by an IVD detection system. This system 100 decreases the difficulty of precisely locating the cuvette window with the light beam, especially in configurations where the cuvettes cannot be clearly seen from above the reaction ring.

Figure 6B:
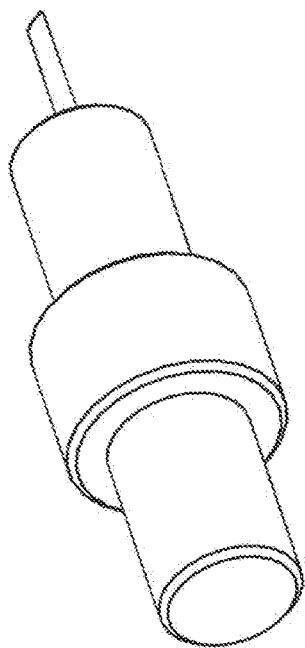
FIG. 6B provides an illustration of a light beam gauge used in some embodiments of the present invention.

Cuvette segment alignment is performed using a variety of components in the system 100. These components include a gauge vertical reaction ring 105 configured with openings that receive a light beam gauge 110. A more detailed view of the light beam gauge 110 is shown in FIG. 6B. As shown in FIG. 6B, the light beam gauge 110 is a cylindrical object with a sharp edge on the end. As described below, the sharp end may be used to create a circular spot on the cuvette window when manually rotated with a small force applied against the cuvette. The light beam gauge 110 may generally be constructed out of any material capable of scoring (i.e., cutting or scratching) the cuvette window to make the circular spot.

Figure 6D:
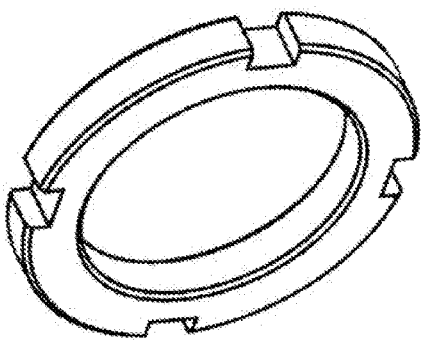
FIG. 6D provides an illustration of a ring lock aperture used in some embodiments of the present invention.
Figure 6A:
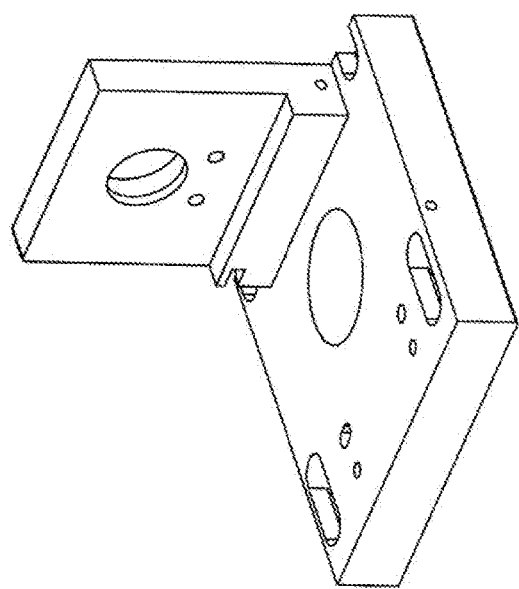
FIG. 6A provides an illustration of a bracket light source photo used in some embodiments of the present invention.
Figure 6C:
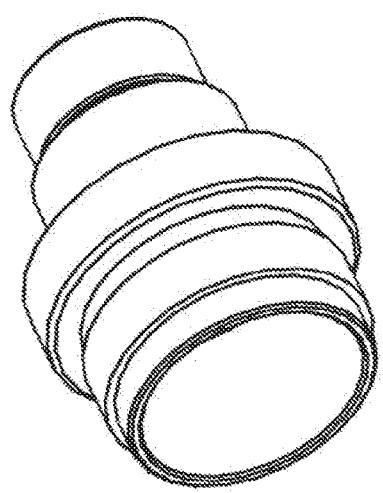
FIG. 6C provides an illustration of an aperture photometer used in some embodiments of the present invention.

The light beam gauge 110 resides in an aperture photometer 120 within a lamp mounting bracket 115. The aperture photometer 120 is secured to the lamp mounting bracket 115 using a ring lock aperture 125. The design of the lamp mounting bracket 115, the aperture photometer 120, and the ring lock aperture 125 are shown in further detail in FIGS. 6A, 6C, and 6D, respectively. In operation of the system 100 shown in FIG. 1, the lamp mounting bracket 115 provides the location of the light beam used for photometric analysis. The lamp mounting bracket 115 holds the aperture photometer 120 at a height corresponding to the actual light source center axis 125 of the photometer. At this height, the aperture photometer 120 allows for the insertion and rotation of the light beam gauge 110 to create the circular spot on the cuvette window.

Figure 2A:
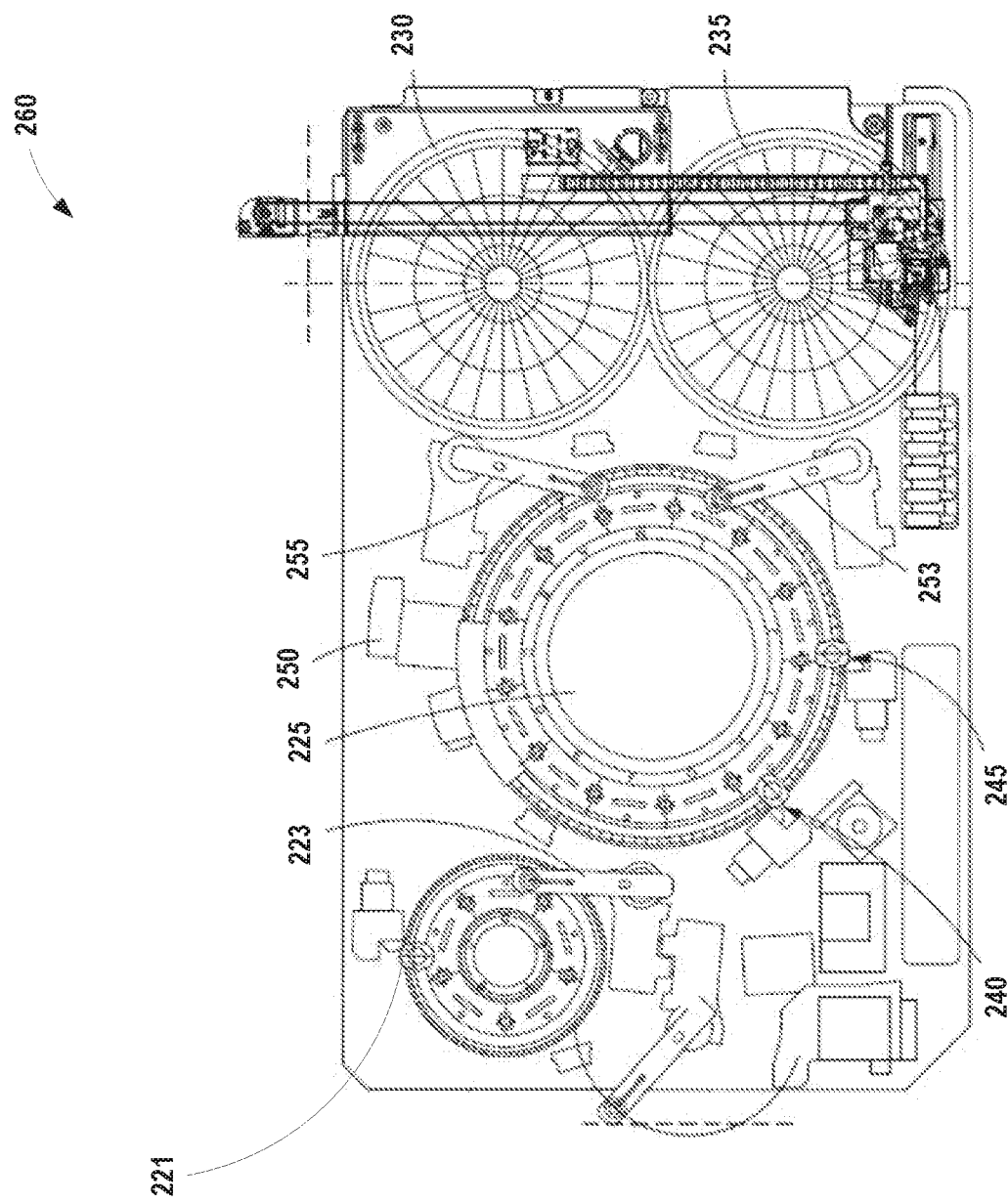
FIG. 2A is a top down view of electromechanical systems for an exemplary analyzer module for use with some embodiments.

FIG. 2A is a top down view of electromechanical systems for an exemplary analyzer module 260 for use with some embodiments. Sample arm 223 is responsible for aspirating a sample portion prepared by dilution mixer 221, moving above a reaction ring 225, and dispensing that sample portion into a cuvette. In some embodiments, reaction ring 225 can include a plurality of concentric rings having cuvettes with samples and reagents. These rings can be moved relative to one another to allow reagents to be aspirated and dispensed into reaction vessels containing samples. In some embodiments, a single ring is used. The reaction ring may include cuvette segment assembly and/or a gauge vertical reaction ring, as described below with respect to FIGS. 2B-2D. Reagents can be added before the sample arrives, or after the sample arrives via reagent arm 235 or reagent arm 255. Reagent servers 230 and 235 include a variety of different reagents, allowing a variety of tests to be performed by analyzer module 260. Reagent arms 253 and 255 move aliquots of reagents from reagent server 235 or reagent server 230, respectively. These aliquots are then dispensed into cuvettes in reaction ring 225. Reaction ring 225 moves cuvettes in a predetermined sequence such that each cuvette reaches reagent mixer 240 or sample mixer 245 for mixing. Once mixed, the reaction between the sample and reagent proceeds in the cuvette. Reaction ring 225 rotates to allow photometer 250 to take photometric measurements of the reaction at predetermined times.

Figure 2B:
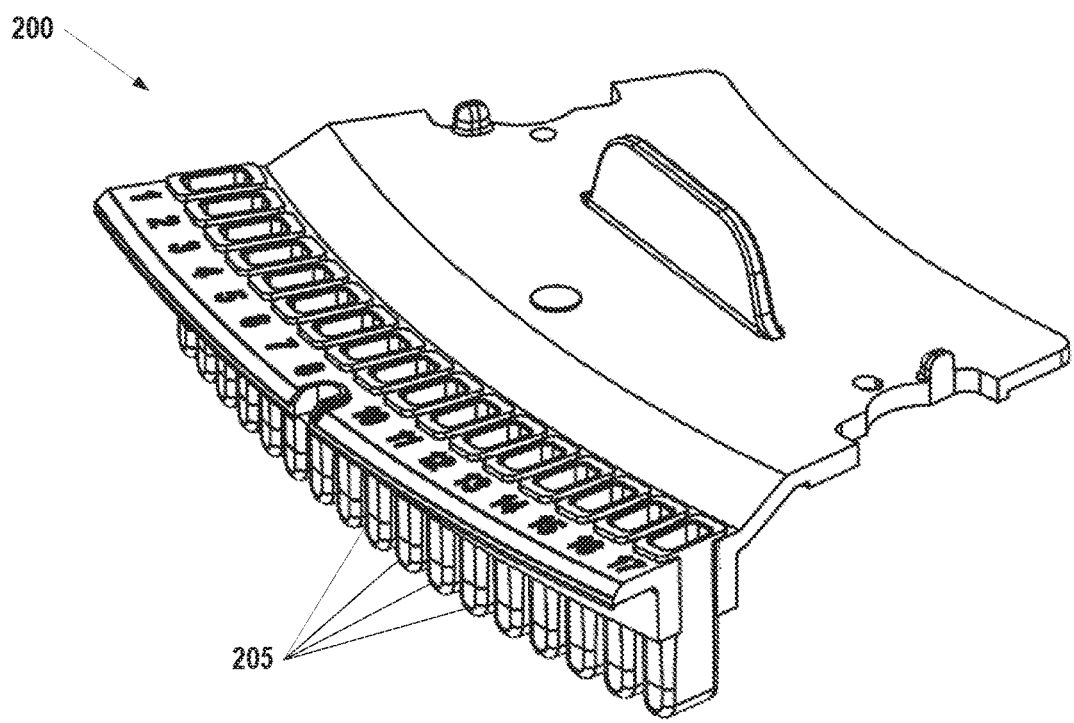
FIG. 2B shows a view cuvette segment assembly with cuvettes installed.
Figure 2C:
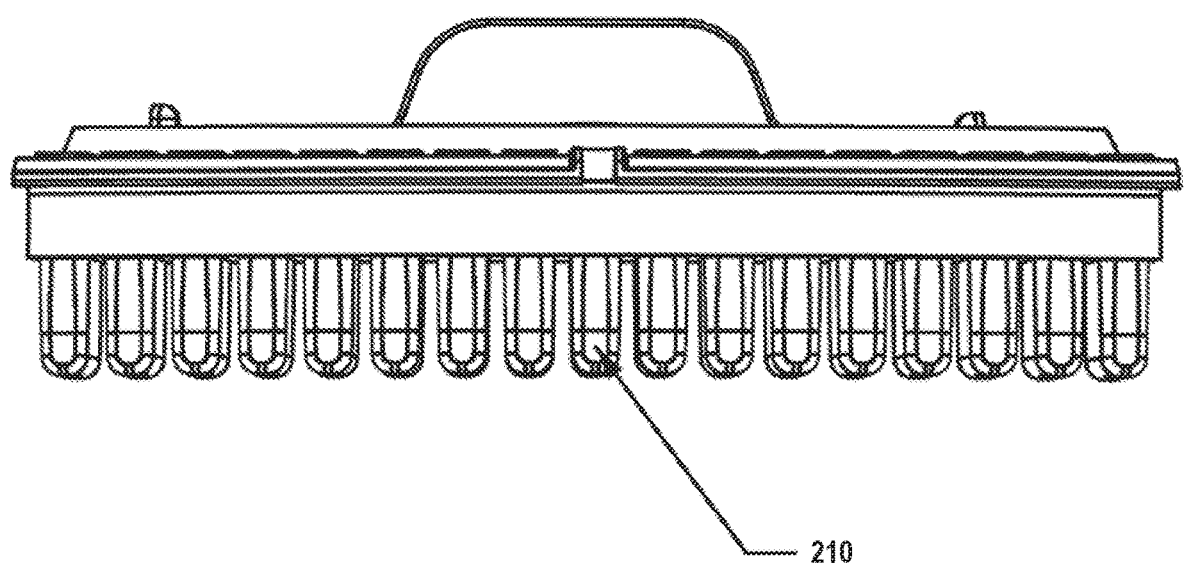
FIG. 2C shows an alternative view of the shown in FIG. 2B.

FIG. 2B shows a view cuvette segment assembly 200 with cuvettes installed (e.g., cuvettes 200). Each cuvette is a small tube designed to hold samples for spectroscopic experiments. Cuvettes are sealed at one end and have a circular cross-section or, as illustrated in FIG. 2B the cross section may be square or rectangular. Square or rectangular cross-sections are generally used to avoid refraction artefacts while making photometric measurements. Various materials may be used to construct cuvettes including, without limitation, optical glass, UV quartz, IR quartz, or sapphire. FIG. 2C shows an alternative view of the shown in FIG. 2B. The view provided in FIG. 2B illustrates that the lower portion of each cuvette includes a small window referred to herein as the "optical area" (e.g., optical area 210). During the photometric measurement, light emitted by the light beam gauge is directed to the optical area of the cuvette.

Figure 2D:
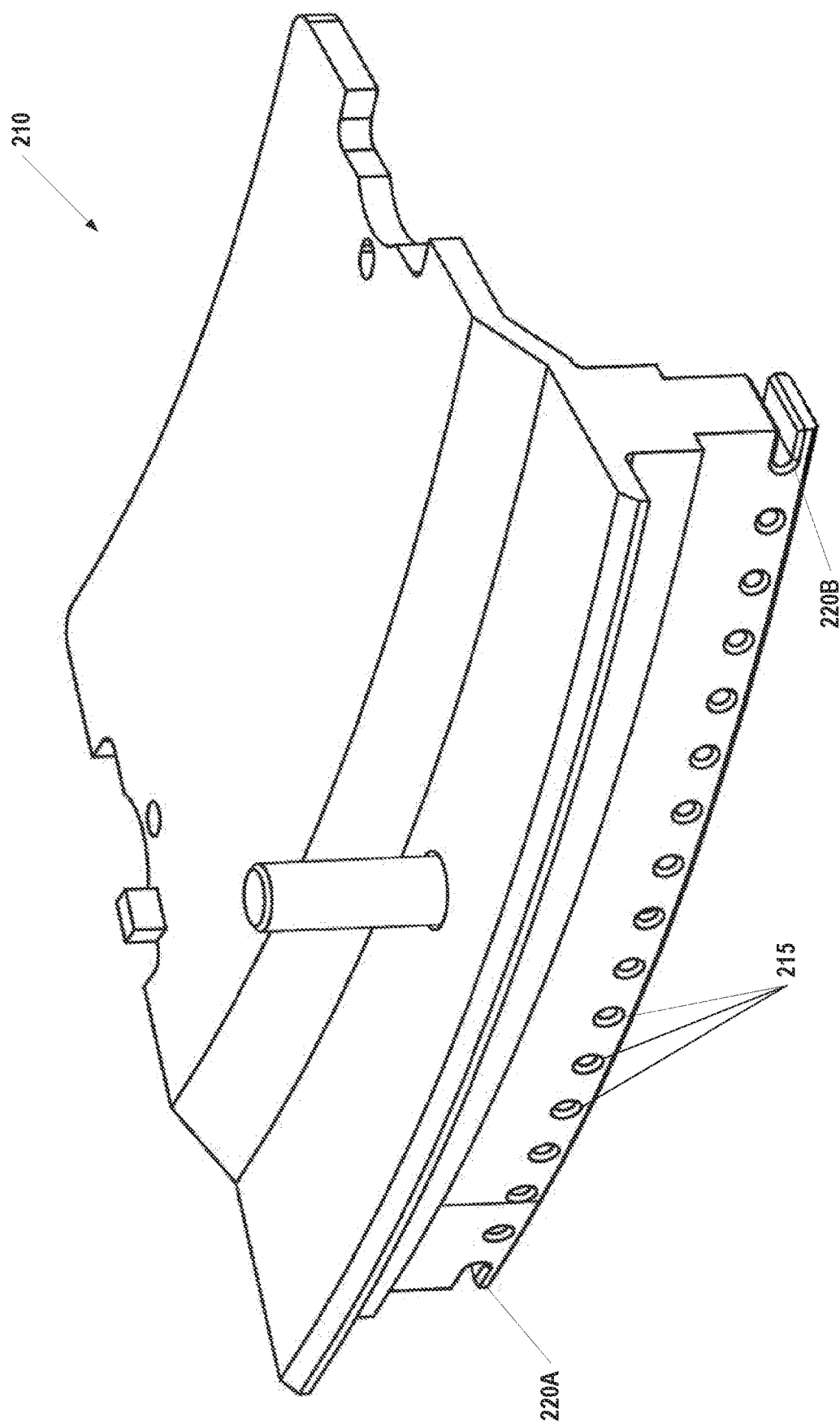
FIG. 2D provides a gauge vertical reaction ring that is designed to represent a cuvette segment assembly holding cuvettes.

FIG. 2D provides a gauge vertical reaction ring 210 that is designed to represent a cuvette segment assembly holding cuvettes (e.g., as shown in FIGS. 2A and 2B). As shown in FIG. 2D, the gauge vertical reaction ring 210 includes a plurality of openings (e.g., openings 215) at positions corresponding to the optical areas of the cuvettes (see FIG. 2B). As shown in FIG. 2D, the openings are located along a line at the front of the gauge vertical reaction ring 210. Each end of the line of openings includes a slot (i.e., end slots 220A and 220B). The light beam gauge (see FIGS. 1 and 6B) is insertable into the openings of the gauge vertical reaction ring and each slot.

Thus, these openings allow the light beam gauge to pass through the gauge vertical reaction ring when the reaction ring is adjusted to the proper height. In operation, the gauge vertical reaction ring 210 is rotated manually or automatically until the light beam gauge engages (i.e., enters) one of the end slots. At this point, the light beam gauge is retracted. Then, the gauge vertical reaction ring 210 is rotated by indexing the reaction ring by a predetermined amount stored in the software of the system 100. During this indexing, the light beam gauge is manually inserted into each of the openings. This assures that the light beam gauge enters the optical area of each individual cuvette in the cuvette segment assembly. Next, the gauge vertical reaction ring 210 is removed from the reaction ring and replaced with a cuvette segment assembly holding cuvettes. Then, for each cuvette in the assembly, the light beam gauge is manually inserted into the aperture photometer and rotated against the optical area of the cuvette to create a visual marking (e.g., a small circle). As an alternative to manual insertion, in some embodiments, a motor may be added to automate insertion as well as other actions performed with the light beam gauge (e.g. rotation).

Figure 3:
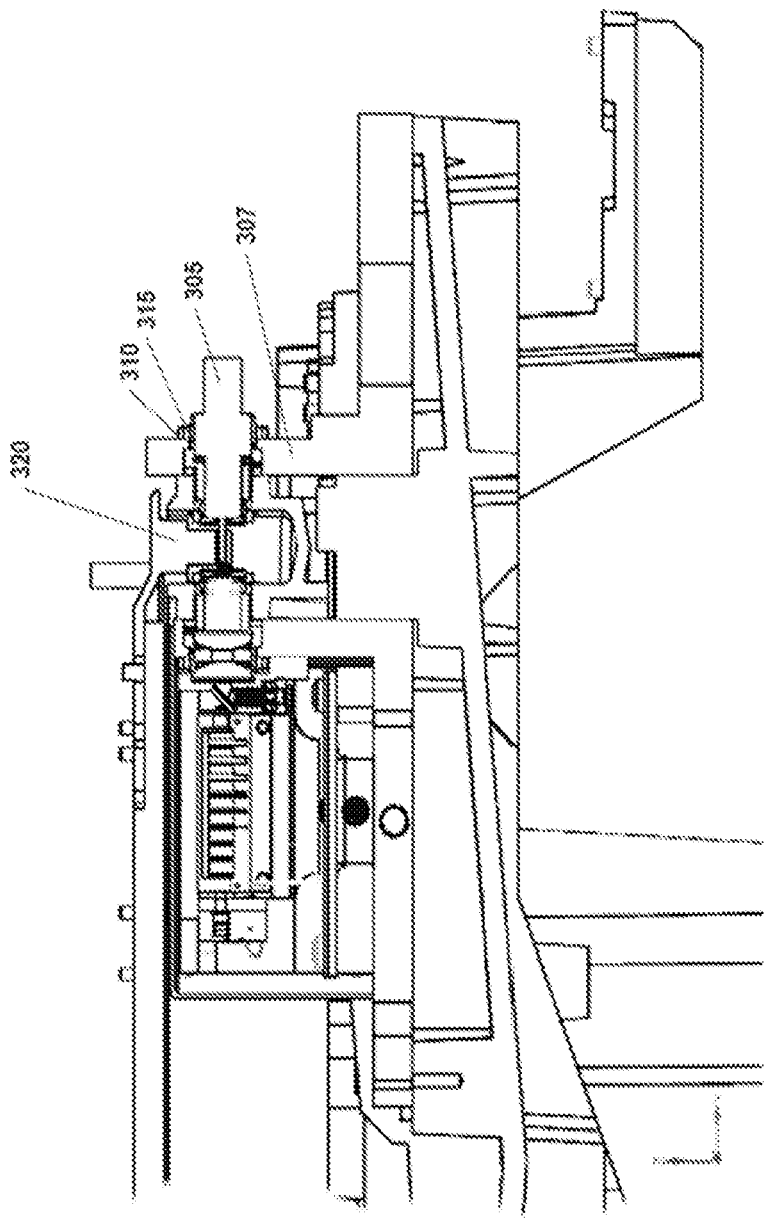
FIG. 3 shows a cross-section of a cuvette alignment system indicating placement of a light beam gauge, according to some embodiments of the present invention.
Figure 4:
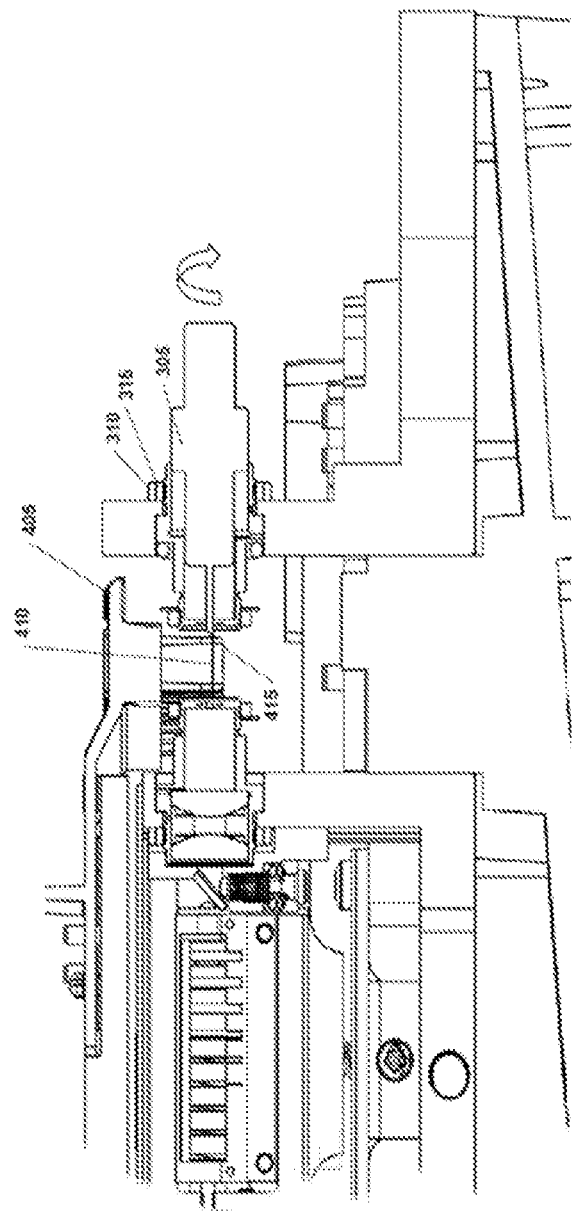
FIG. 4 shows a cross-section of a cuvette alignment system indicating rotation of a light beam gauge against a cuvette, according to some embodiments of the present invention.
Figure 5:
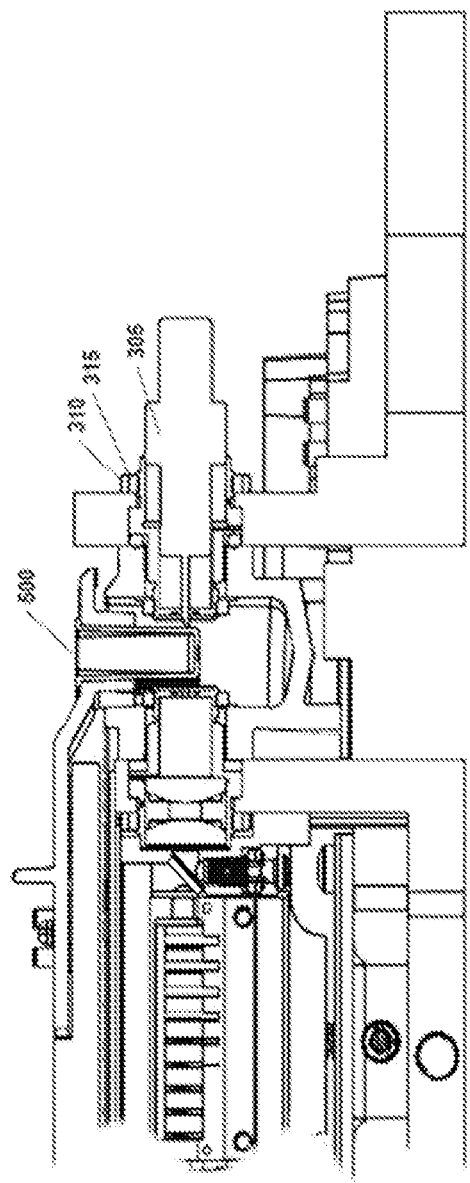
FIG. 5 shows a cross-section of a cuvette alignment system indicating placement of a reaction ring segment assembly, according to some embodiments of the present invention.

FIGS. 3-5 provide additional views of the IVD system with a gauge vertical reaction ring 320 installed, according to some embodiments. FIG. 3 shows a cross-section of a cuvette alignment system, according to some embodiments of the present invention. In this example, an aperture photometer 315 is attached to the lamp mounting bracket 307 to hold a light beam gauge 305 in place at the light source center axis (see FIG. 1). The ring lock aperture 310 shown in FIG. 3 holds the aperture photometer 315 in place, allowing the light beam gauge 305 to score cuvettes in the gauge vertical reaction ring 320 accordingly. One or more shims may be added, as needed, to provide proper alignment of the gauge vertical reaction ring 320 with the light beam gauge 305. Once the gauge vertical reaction ring 320 is properly aligned, the light beam gauge 305 is inserted into the openings and end slots (see FIG. 2D) in the gauge vertical reaction ring 320.

Next, with the cuvette segment in place, the light beam gauge 305 can be rotated against the cuvette to score the optical area. This rotation, along with the placement of the cuvette segment 405, is illustrated in FIG. 4. As shown, the light 410 emitted by the light beam gauge 305 travels through the optical area 415 of the cuvette that is currently aligned with the light beam gauge 305. Finally, FIG. 5 shows the final configuration of the system after the cuvette segment assembly 500 has moved into the location where measurements will be performed.

To summarize the techniques described above, FIG. 7 shows a flowchart which describes a method of aligning a reaction ring in an analyzer system using a gauge vertical reaction ring at least one end slot, according to some embodiments. Starting at step 705 a light beam gauge is inserted into an aperture operable to hold the light beam gauge at a height corresponding to a photometer included in the analyzer system (e.g., the light source center axis of the photometer). At step 710, the gauge vertical reaction ring is placed on the reaction ring of the analyzer. Next, at step 715, the gauge vertical reaction ring is rotated on the reaction ring until the light beam gauge engages the end slot to confirm alignment of the reaction ring with the photometer.

Figure 7:
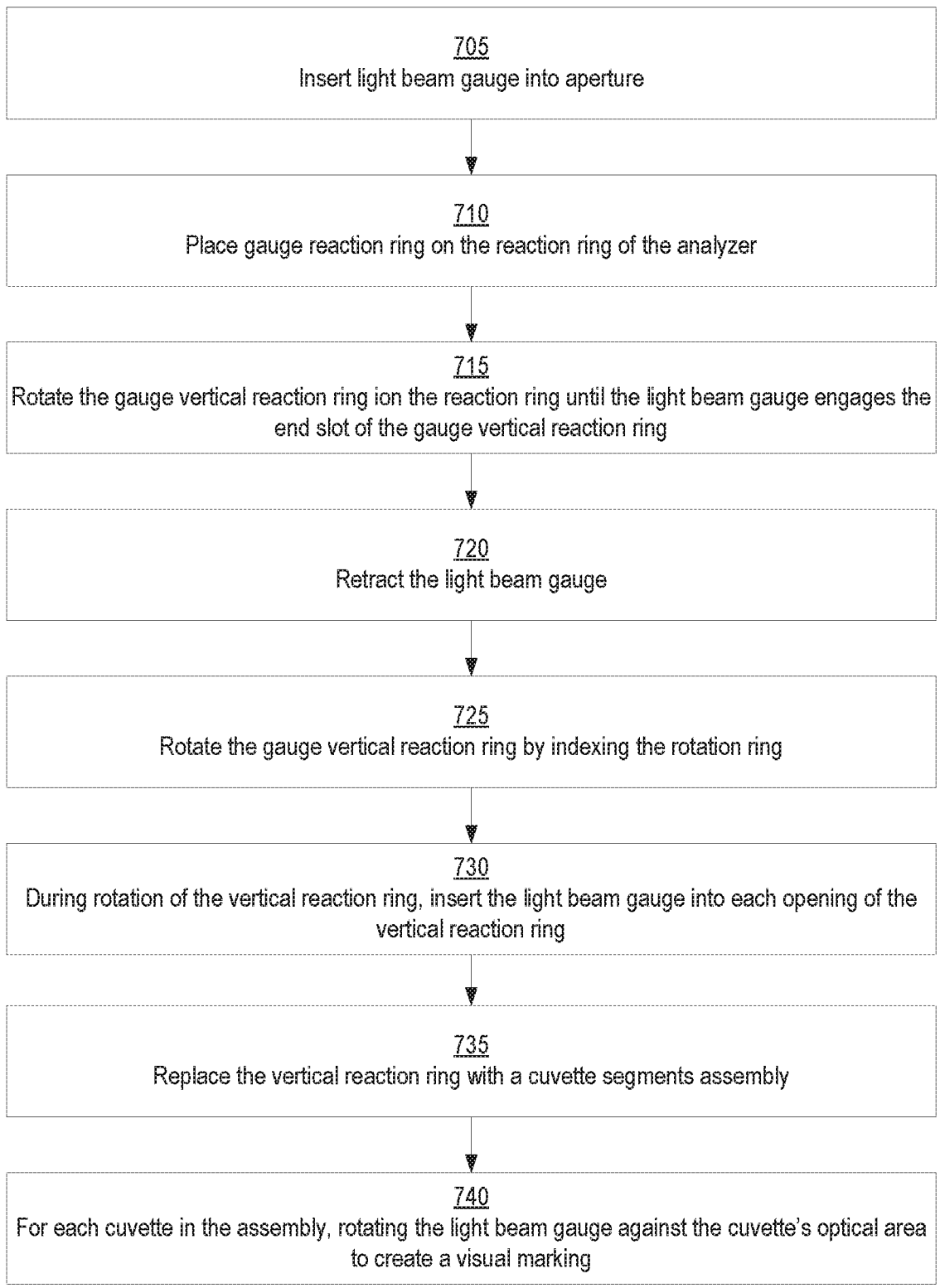
FIG. 7 shows a flowchart which describes a method of aligning a reaction ring in an analyzer system using a gauge vertical reaction ring at least one end slot, according to some embodiments.

Continuing with reference to FIG. 7, at step 720, the light beam gauge is retracted from the aperture, for example, by a user manually pulling the light beam gauge in a direction away from the reaction ring. The light gauge can be removed altogether or simply retracted until the gauge vertical reaction ring can freely rotate without contacting the light beam gauge. Next, at step 725, the gauge vertical reaction ring is rotated by indexing the reaction ring using the analyzer system software. During rotation of the gauge vertical reaction ring, as shown in step 730, the light beam gauge is inserted into each of the openings of the gauge vertical reaction ring to further confirm alignment of the reaction ring with the photometer during the indexing procedure.

At step 735, the vertical reaction ring is replaced on the reaction ring with a cuvette segments assembly comprising a plurality of cuvettes (see FIGS. 2A and 2B). Finally at step 740, for each cuvette in the cuvette segments assembly, the sharp point of the light beam gauge is rotated against an optical area of the cuvette to create a visual marking on the optical area.

The embodiments of the present disclosure may be implemented with a combination of hardware and software. In addition, functionality employed by the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

The functions and process steps herein may be performed automatically, or wholly, or partially in response to user command. An activity (including a step) performed automatically is performed in response to one or more executable instructions or device operations without user direct initiation of the activity.

The systems illustrated in the figures are not exclusive. Other systems may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers, and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A method of aligning a reaction ring in an analyzer system using a gauge vertical reaction ring comprising at least one end slot, the method comprising:
    inserting a light beam gauge into an aperture operable to hold the light beam gauge at a height corresponding to a photometer included in the analyzer system; and
    rotating the gauge vertical reaction ring on the reaction ring until the light beam gauge engages the end slot to confirm alignment of the reaction ring with the photometer.

2. The method of claim 1, wherein the gauge vertical reaction further comprises a plurality of openings and the method further comprises:
    retracting the light beam gauge from the aperture;
    rotating the gauge vertical reaction ring by indexing the reaction ring; and
    during rotation of the gauge vertical reaction ring, inserting the light beam gauge into each of the openings of the gauge vertical reaction ring to confirm alignment of the reaction ring with the photometer.

3. The method of claim 2, wherein the light beam gauge comprises a sharp point and the method further comprises:
replacing the vertical reaction ring on the reaction ring with a cuvette segments assembly comprising a plurality of cuvettes; and
for each cuvette in the cuvette segments assembly, rotating the sharp point of the light beam gauge against an optical area of the cuvette to create a visual marking on the optical area.

4. The method of claim 3, wherein the light beam gauge is manually rotated against the optical area of the cuvette by a user.

5. The method of claim 1, wherein the indexing of the reaction ring is performed automatically by the analyzer system.

6. The method of claim 1, wherein the height corresponding to the photometer corresponds to a light source center axis of the photometer.

7. A method of aligning a reaction ring in an analyzer system using a gauge vertical reaction ring comprising a plurality of openings, the method comprising:
rotating the gauge vertical reaction ring on the reaction ring by indexing the reaction ring; and
during rotation of the gauge vertical reaction ring, inserting a light beam gauge through an aperture into each of the openings of the gauge vertical reaction ring to confirm alignment of the reaction ring with a photometer included in the analyzer system, wherein the aperture is operable to hold the light beam gauge at a height corresponding to a photometer included in the analyzer system.

8. The method of claim 7, wherein the gauge vertical reaction ring comprises at least one end slot and the method further comprises:
prior to indexing the reaction ring, inserting the light beam gauge through the aperture and rotating the gauge vertical reaction ring until the light beam gauge engages the end slot to confirm alignment of the reaction ring with the photometer.

9. The method of claim 8, wherein the light beam gauge comprises a sharp point and the method further comprises:
replacing the vertical reaction ring on the reaction ring with a cuvette segments assembly comprising a plurality of cuvettes; and
for each cuvette in the cuvette segments assembly, rotating the sharp point of the light beam gauge against an optical area of the cuvette to create a visual marking on the optical area.

10. The method of claim 9, wherein the light beam gauge is manually rotated against the optical area of the cuvette by a user.

11. The method of claim 7, wherein the indexing of the reaction ring is performed automatically by the analyzer system.

12. The method of claim 7, wherein the height corresponding to the photometer corresponds to a light source center axis of the photometer.

13. A system for aligning a reaction ring in an analyzer system, the system comprising:
a gauge vertical reaction ring installable on the reaction ring, wherein the gauge vertical reaction ring comprises a plurality of openings at positions corresponding to optical areas associated with the cuvettes in a cuvette segments assembly; and
a light beam gauge comprising an end portion insertable into the plurality of openings.

14. The system of claim 13, further comprising:
a bracket light source photo configured to hold the light beam gauge at a height corresponding to a light source center axis corresponding to a photometer included in the analyzer system.

15. The system of claim 14, further comprising:
an aperture photometer configured to hold the light beam gauge in the bracket light source photo.

16. The system of claim 15, further comprising:
a ring lock aperture configured to secure the aperture photometer within the bracket light source photo.

17. The system of claim 15, wherein the aperture photometer is an aperture 1.5 mm photometer.

18. The system of claim 14, wherein the gauge vertical reaction ring further comprises one or more end slots operable to engage the light beam gauge when the light beam gauge is placed in the bracket light source photo and the gauge vertical reaction ring is rotated on the reaction ring.

19. The system of claim 13, wherein each of the plurality of openings is circular.

* * * * *